United States Patent [19]
Stokes et al.

[11] Patent Number: 5,252,228
[45] Date of Patent: Oct. 12, 1993

[54] CYTOCENTRIFUGATION DEVICE, APPARATUS, AND METHOD

[75] Inventors: Barry O. Stokes; Carmelo G. Quirante, both of Logan, Utah

[73] Assignee: Wescor, Inc., Logan, Utah

[21] Appl. No.: 788,310

[22] Filed: Nov. 5, 1991

[51] Int. Cl.⁵ .............................................. B01D 33/15
[52] U.S. Cl. .................................... 210/781; 210/782; 210/361; 422/72; 422/101
[58] Field of Search ............... 210/515, 516, 518, 361, 210/512.1, 781, 782; 422/72, 101

[56] References Cited
U.S. PATENT DOCUMENTS

| | | | |
|---|---|---|---|
| 4,391,710 | 7/1983 | Gordon | 210/361 |
| 4,423,699 | 1/1984 | Boeckel et al. | 118/52 |
| 4,428,323 | 1/1984 | Wells | 118/52 |
| 4,574,729 | 3/1986 | Wells | 118/52 |
| 4,678,579 | 7/1987 | Griffin | 210/477 |

OTHER PUBLICATIONS

A Slide Centrifuge Journal of Laboratory Clinical Medicine 1966, vol. 68, 494–501.
Ames Makes Cytocentrifugation Trade Literature 1987.

*Primary Examiner*—Robert A. Dawson
*Assistant Examiner*—David Reifsnyder
*Attorney, Agent, or Firm*—Mallinckrodt & Mallinckrodt

[57] ABSTRACT

Cytocentrifugation apparatus is improved by providing centrifuging devices with a plurality of liquid-receiving chambers arranged serially along and opening into an elongate conduit leading to and terminating within a filter-pad-holder so that a filter-pad-prewetting liquid can be passed along such conduit and into a liquid-flow opening of a filter pad held by such holder in advance of passage along said conduit and through such liquid-flow opening in the filter pad of a cell-carrying liquid sample during a centrifugation run of the apparatus. Retention of prewetting liquid in the filter pad around the sample liquid flow helps to prevent loss of cells to the filter pad. Various other structural modifications of the cytocentrifugation device and filter pads used therewith also help to prevent loss of cells to the filter pad.

14 Claims, 3 Drawing Sheets

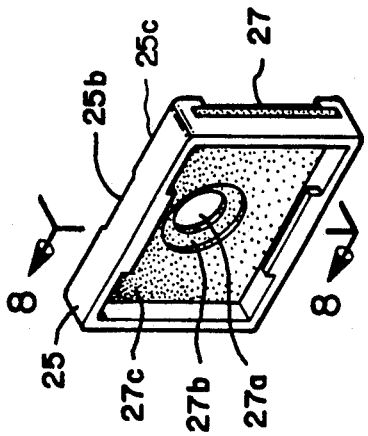
FIG. 5
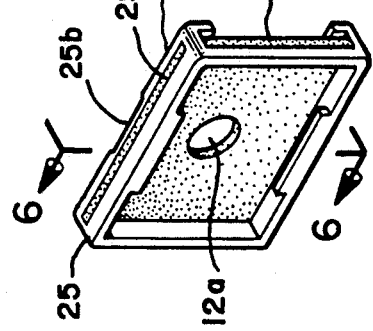
FIG. 6
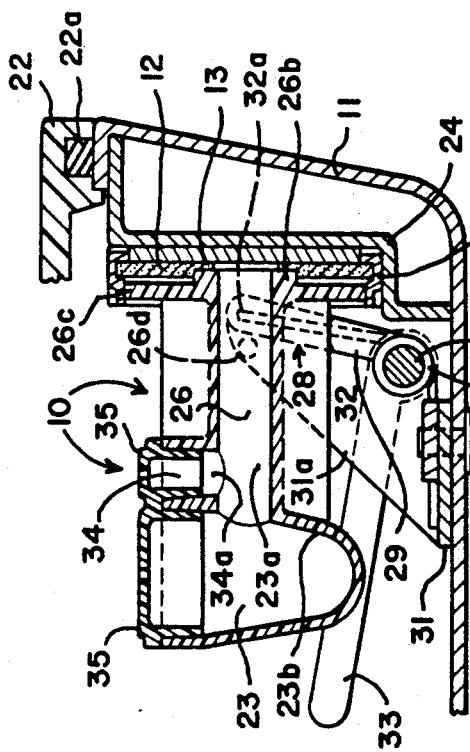
FIG. 3
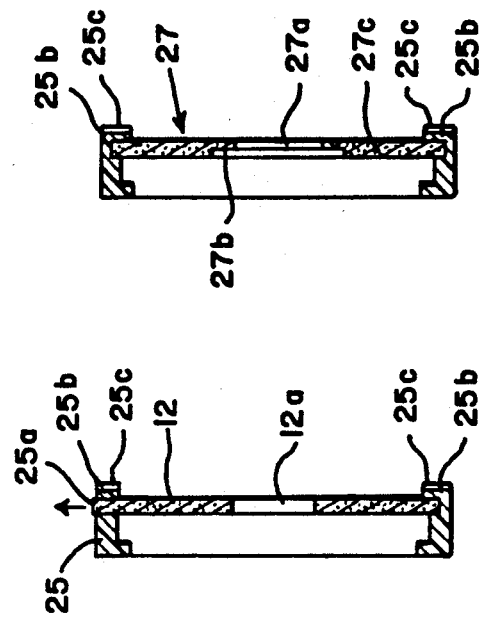
FIG. 7
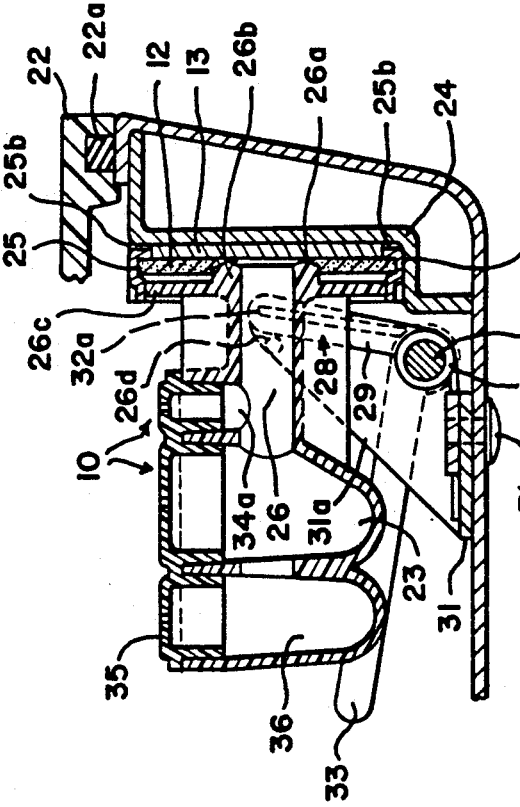
FIG. 4
FIG. 8

CYTOCENTRIFUGATION DEVICE, APPARATUS, AND METHOD

BACKGROUND OF THE INVENTION

Field:

The invention is in the general field of medical laboratory equipment and is particularly concerned with cytocentrifuges, i.e. apparatus for centrifugally depositing on microscope slides cells from a liquid suspension of same and with methods of using such apparatus.

State of the Art:

Apparatus of the type concerned have been developed heretofore and are widely used. Perhaps the best known cytocentrifuge is the "Cytospin" produced by or under the auspices of Shandon Southern Products Limited, Rancorn, England, as shown by Gordon U.S. Pat. No. 4,391,710 of Jul. 5, 1983 and by Griffin U.S. Pat. No. 4,678,579 of Jul. 7, 1987. There, as in other apparatus of the type concerned, a liquid suspension of cells to be deposited on a microscope slide is placed in a sample chamber of a cytocentrifuge device, normally one adapted for installation in a centrifuge that is adapted to receive a plurality of such devices, each equipped with a sample chamber, a filter pad holder, and a slide holder, so multiple microscope slides can be prepared at the same time, such liquid suspension of cells being passed by centrifugal force from sample chamber to slide surface through an opening in a filter pad that is clamped against the receiving surface of the slide for both sealing so far as possible against lateral passage and consequent loss of the cell-carrying liquid with its cells and for absorbing the liquid component of such cell-carrying liquid upon deposit of the cells on the slide.

Alan J. Gordon, inventor in the aforesaid U.S. Pat. No. 4,391,710, improved pre-existing machines for Shandon in various respects, primarily by incorporating slide and filter card clamping means as part of a sample chamber unit that is removable unitarily (with clamping means) from a centrifuge rotor of the cytocentrifuge.

Prewetting of the liquid-absorbent filter pad has been resorted to in some instances prior to centrifugation to minimize attraction for the cell-carrying liquid sample as it passes toward the microscope slide, with consequent diversion into the filter pad with loss of cells before they have a chance to adhere to the slide.

Also, utilizing a sample chamber having depth that normally dams against liquid outflow except under centrifuging action has been tried in the past for both centrifugal chemical analyzers and cytocentrifuges, see particularly the N. G. Anderson article entitled "The Development of Fast Analyzers", Z. Anal. Chem. 257–271 (1972), and Wells U.S. Pat. No. 4,428,323 of Jan. 31, 1984, respectively.

Prior to the development of cytocentrifuges utilizing centrifugal force to propel a sample of a cell-carrying liquid toward and onto a microscope slide, application of cells onto microscope slides was accomplished by sedimentation techniques utilizing gravity to flow samples of a cell-carrying liquid onto the slides, see the article in *ActaCytologica* 8, 234–241 (1964) by G. Th. A. M. Bots et al.

Present day cytocentrifuges do significantly better than the sedimentation technique. This is accomplished by the use of high centrifugal speeds, wherein sedimentation velocity of cells suspended in the cell-carrying liquid onto the slide is considerably greater than the hydraulic force exerted laterally of the slide face on which the cells are to be deposited.

In practice, present systems employ a trade-off between filter pad thickness governing liquid-holding capacity and a conveniently handled clamping force holding the filter pad against the slide during centrifugation. This places practical constraints on the range of performance characteristics of current systems. For example, if a very slow liquid flow rate into the filter pad is desired, with a convenient clamping spring force, a very thin filter pad must be employed. Under these conditions, the quantity of the sample will be limited to the volume of liquid that such filter pad will hold. If a larger quantity of the sample liquid is involved, a relatively thick filter pad should be employed to receive and retain the greater quantity of liquid component of the liquid sample, but then the flow rate can be too fast to allow good cell recovery.

Loss of cells is also suffered in the transition from the stationary state of the loaded sample chamber to the ultimate steady state speed of operation. Such loss is most severe when the sample liquid comes into contact with the filter pad prior to initiation of centrifugation. Lateral flow into the filter without centrifugation takes place as permitted by the clamping force, filter characteristics, and system geometry. With no centrifugal force to sediment the cells against the slide, the cells tend to flow into the filter with the liquid. If a large fraction of the sample flows into the filter under these conditions, a correspondingly large fraction of the cells can be lost. It has therefore been recognized that some means must be provided to prevent premature contact of the liquid sample with the filter pad. Alan J. Gordon (U.S. Pat. No. 4,391,710) accomplished this for Shandon by providing a tilting chamber. John Wells (U.S. Pat. No. 4,428,323) on the other hand provided a well for the sample liquid as a dam against premature release of such sample, as N. G. Anderson had done for the so-called "Fast Analyzer". The force required, and hence the speed of delivery, is determined by the depth of the well and the slope of the dam.

With the above provisions, transitional cell loss is significantly reduced but it still occurs to an undesirable extent. Even with the system of John Wells, upon start up, the liquid is forced over the dam and into the flow passage leading therefrom. Cell-carrying sample liquid rushes into the empty flow passage on start up. Since the cells are uniformly suspended in the sample liquid, the initial contact with the filter pad will cause absorption of cell-containing liquid.

Another source of cell loss is during wet fixation after the cells have been collected on the slide. Normally, the collected cells are sprayed with, or the slide is immersed in, an aqueous alcohol fixative solution. Residual liquid on the slide interacts with the fixative solution and, together with the forces involved in applying the solution, often results in dislodging of otherwise adherent cells from the slide.

Some manufacturers recommend addition of fixative liquid into the sample chamber after addition of the cell-containing liquid sample so that cells will be fixed during centrifuging. However, there is no provision for separating the fixative from the sample and cells become fixed prior to collection on the slide. This results in cells which do not properly flatten and therefore do not adhere well to the slide, thus producing poor morpholog and cell loss. No equipment presently exists which provides for in-situ fixation during centrifuging following cell sedimentation.

SUMMARY OF THE INVENTION

The present invention further improves cytocentrifuge apparatus and methods in order to achieve maximum capture of cells by the microscope slide toward which the cell-carrying liquid is passed from the corresponding sample chamber under the impetus of centrifugal force while taking up in a satisfactory manner the liquid component of the liquid sample following cell deposition on the slide.

This has been accomplished by providing an improved device for use with a cytocentrifuge, such device having a plurality of liquid-receiving chambers serially related and communicating with and along a conduit in common that leads to a holder for a microscopic slide provided in part by the device and in part by the clamping means carried by the rotor and across the discharge end of the conduit so as to be within such slide holder is interposed means for receiving and holding, in fluid-sealing relationship with the confronting face of a slide held by the slide holder, a liquid-absorbent filter pad. There are at least two of the liquid-receiving chambers arranged serially along the conduit, the devices themselves being arranged in usual multiple fashion in the rotor of a cytocentrifuge machine.

The chambers can be of any type arranged for sequential discharge of their contained liquid into the conduit under centrifuging conditions so long as there are at least two of them. Preferably the chamber located closest in line to the filter pad holder and to the microscope slide holder in each device is positioned above the conduit, with its bottom open and opening into the conduit. A filter pad prewetting solution is preferably placed in the chamber for wetting the filter pad in advance of the passing therethrough of the cell-carrying liquid sample and for providing a liquid barrier between the cell-carrying sample liquid and the filter pad. The sample liquid is preferably placed in the second chamber in line that extends below the conduit as a well for damming against outflow of liquid into the conduit except by the exercise of centrifugal force on such liquid.

It can be seen that, if a filter-pad-prewetting liquid is placed in the chamber that is located closest to the filter pad holder and the slide holder of the cytocentrifuging device, it will precondition the filter pad by prewetting it prior to contact therewith of the cell-carrying liquid sample. When the cell-carrying liquid sample reaches the filter, such filter will have already absorbed advance-flowing liquid that is devoid of cells, and will further restrict lateral flow of the cell-carrying liquid that follows.

Since the cell-carrying liquid sample discharges into and flows through the conduit before the prewetting liquid is completely absorbed, the residual prewetting liquid forms a barrier which prevents the cell-carrying liquid from contacting the filter pad until the final steady-state rotor speed is achieved. At such final rotor speed, maximum sedimentation velocity of the cells will have been achieved, thus minimizing lateral diversion of cells into the filter pad.

Filter pad fabrication may be such, in accordance with the invention, that it is still capable of absorbing the liquid component of the liquid sample even if thinner than usual around the opening through which the sample liquid flows, following extraction of cells therefrom by deposition on and retention by the surface of the slide. To this end, a novel, dual-thickness filter pad is employed which is relatively thin marginally of the liquid flow opening and is otherwise relatively thick, this being achieved either by compressing a single thickness sheet of filter pad material marginally of the opening therethrough or fabricating the filter pad from two sheets of filter pad material with only the desired thicker portion of the final filter pad being double thickness. Alternatively, a usual single thickness filter pad can be used with the provision of a filter-pad-indenting ring as the clamping face of the filter pad clamp, so that the flow rate of the liquid component of the cell-carrying liquid sample into the filter pad will be restricted. Such an indenting ring can be employed advantageously with any type of filter pad.

Further structural features of the invention that contribute to convenience of use of the cytocentrifuge are:

1. The provision of each device with a filter pad holder that is integrally molded with the body of the device from a plastic material for either removal and replacement of a used filter pad when the device is to be reused, or with filter pad molded or tightly held therein for discard with the entire device following use, this being accompanied by means permitting slide removal without distributing cells deposited thereon.

2. Provision of a spring-actuated clamping mechanism for the filter pad holder and slide holder, which is easily opened by means of a manually operated lever arm and which may be and preferably is securely, rather than removably, mounted on the rotor for repeated use with replacement cytocentrifuge sample devices. Such clamping means is prevented from contacting and possibly breaking a glass slide in the absence of the cytocentrifugation device, which is normally not installed on the rotor until a glass slide is placed in the portion of the slide holder provided by the clamping means.

3. Provision for automatically aligning the filter pad relative to the conduit through which the cell-carrying sample liquid and other liquid or liquids are passed.

The multi-chambered device of the invention provides not only for prewetting of the filter pad in advance of the cell-carrying sample liquid reaching the filter pad and the microscope slide, but enables the cells to be fixed on the slide as part of a continuing centrifuging operation. Thus, a fixative liquid may be introduced into the chamber of the plurality of chambers that follows the sample chamber, so that there is sequential flow therefrom following flow of the liquid sample.

From a method standpoint, the invention provides a procedure in the us of the apparatus comprising the steps of placing a cell-carrying liquid sample in a chamber of the plurality of chambers and placing either a filter-pad-wetting liquid in the first in line of the series of chambers toward the filter pad and slide holder or a fixative solution in a chamber that follows in line the liquid sample receiving chamber, and then operating the cytocentrifuging apparatus.

THE DRAWINGS

The best mode presently contemplated for carrying out the invention in actual practice is illustrated in the accompanying drawings, in which:

FIG. 1 represents a view in top plan of a cytocentrifuging rotor of the invention having multiple cytocentrifugation devices therein;

FIG. 2, a fragmentary vertical section taken on the line 2-2 of FIG. 1 and drawn to a somewhat larger scale showing the cytocentrifuging rotor of FIG. 1 as mounted for use on a general purpose centrifuge machine;

FIG. 3, an enlarged, right-hand, fragmentary portion of FIG. 2, showing only the cytocentrifuging device and the clamping means as secured on the rotor;

FIG. 4, a view corresponding to that of FIG. 3, but of an embodiment having a third chamber similar to the second chamber of FIG. 2 and arranged in series with the two chambers of FIG. 2;

FIG. 5, a detail view in perspective drawn to the scale of FIGS. 3 and 4, and looking toward the front of and showing a filter pad placed in filter pad holding means provided as a part of the device of FIGS. 3 and 4 and constructed to receive and shown as holding a replaceable filter pad of conventional type;

FIG. 6, a vertical section taken on the line 6—6 of FIG. 5 and drawn to a larger scale;

FIG. 7, a view corresponding to that of FIG. 5 but showing a completely disposable filter pad receptacle and filter pad, the filter pad having a thin portion marginal to the center opening and being thick otherwise in accordance with one aspect of the invention; and FIG. 8, a vertical section taken on the line 8—8 of FIG. 7 and drawn to the larger scale of FIG. 6.

DETAILED DESCRIPTION OF THE ILLUSTRATED EMBODIMENTS

In the form illustrated in FIGS. 1–4, as well as FIGS. 5 and 6, cytocentrifuging devices 10 of the invention are received by and mounted side-by-side in a cytocentrifuging rotor 11. Each of the devices 10 are multi-chambered in the sense that there are a plurality, in this instance two, liquid-receiving chambers arranged in line successively to discharge sequentially into a conduit in common that leads to holding means for a filter pad 12, FIGS. 5 and 6, or 27, FIG. 5 and and to holding means for a microscope slide 13, FIGS. 3 and 4, in separate clamping means secured in rotor 11.

Figure 1:
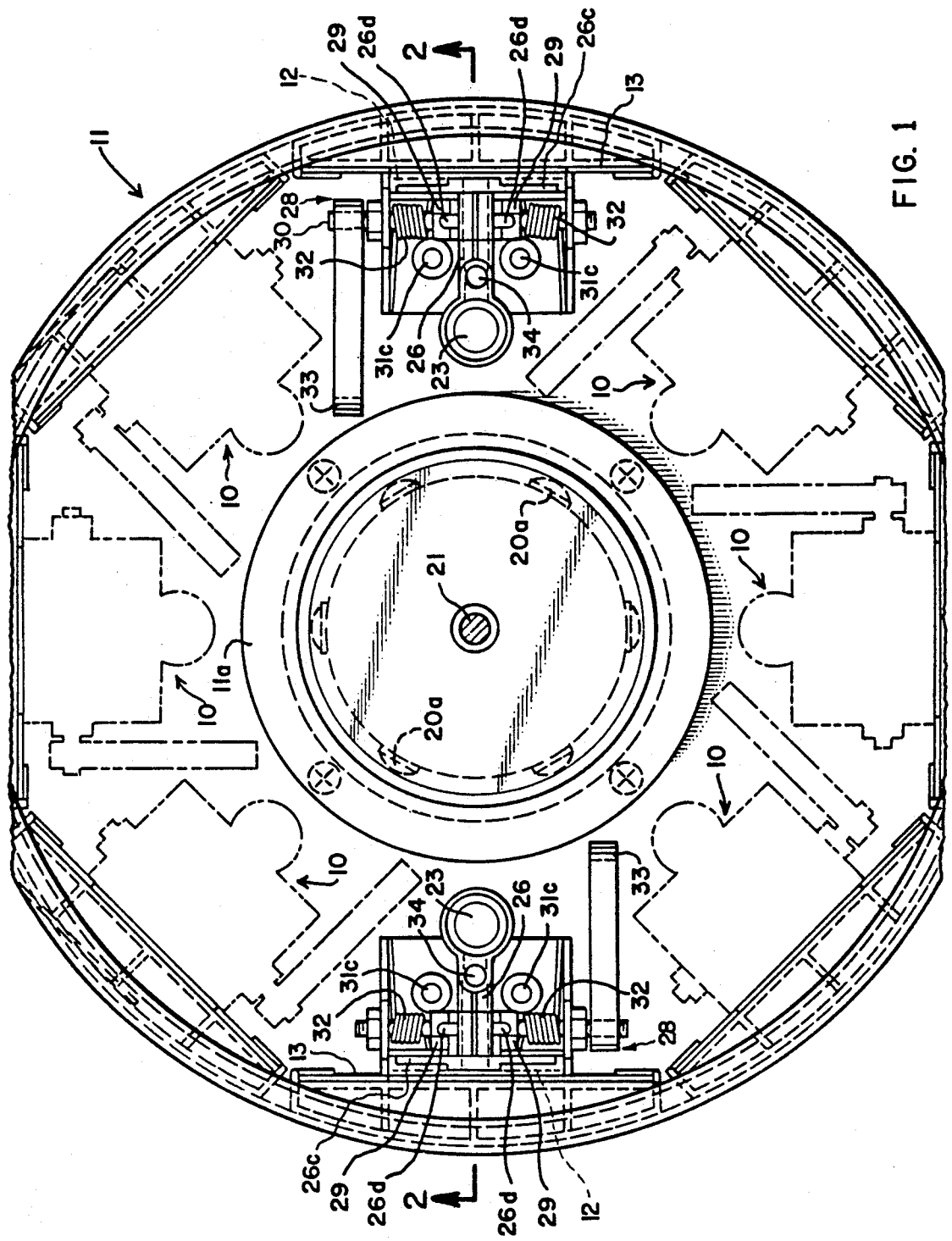
Figure 2:
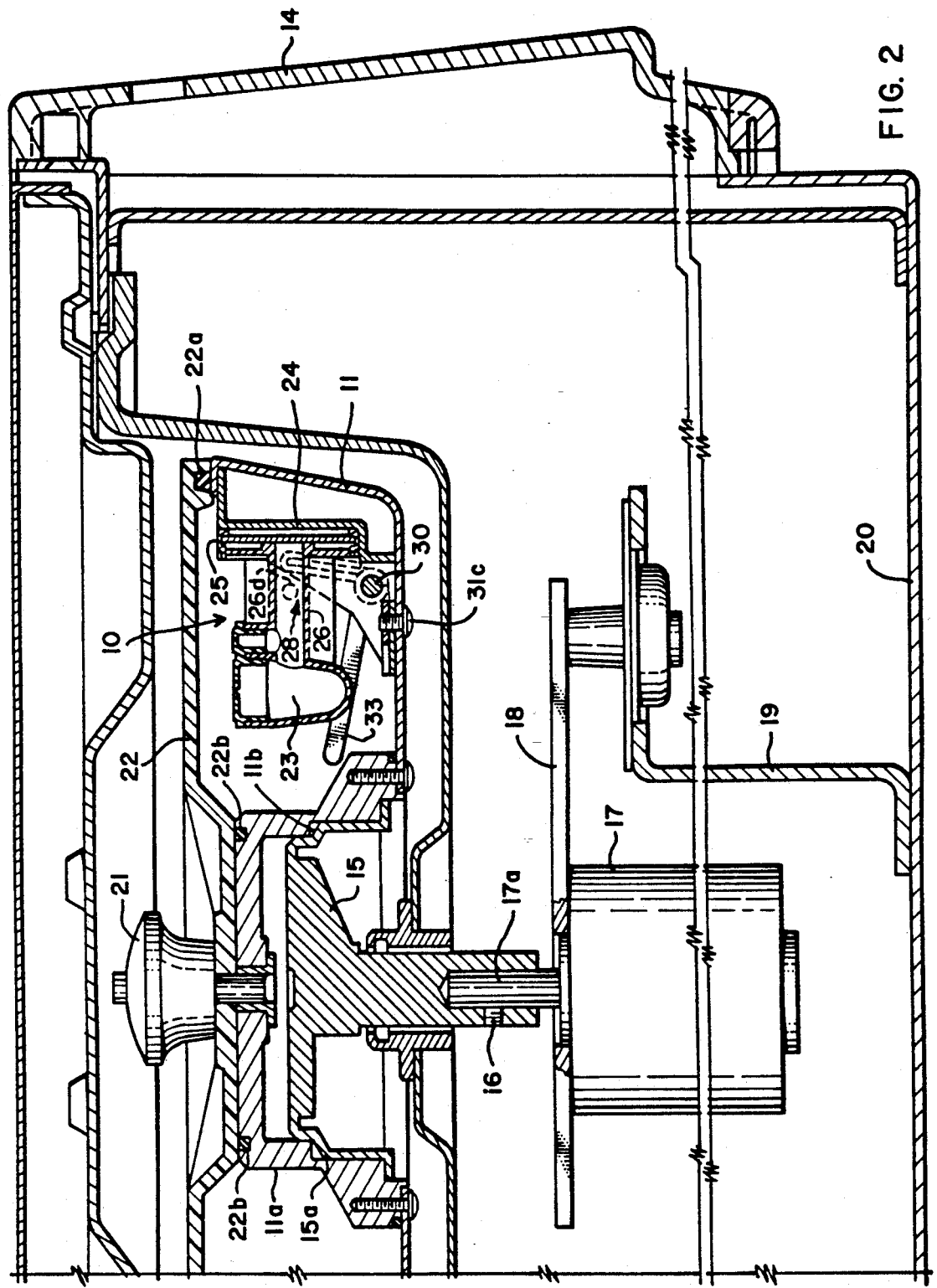

Rotor 11 is removably and replaceably mounted for rotation on a general purpose centrifuge machine 14, FIG. 2, which, in this instance, is provided with a hub 15 secured by a set-screw 16 to the drive shaft 17a of an electric motor 17 that is mounted by a bracket 18 on a standard 19 of a housing 20. Hub 15 is received by a recessed fitting 11a opening into the underside of rotor 11 and provided with a circumferential series of grooves 11b for receiving a corresponding series of ribs 15a projecting from hub 15. A grasping knob 21 projects upwardly from a cover 22 for rotor 11 to enable convenient removal and replacement of such rotor on centrifuge machine 14. O-rings 22a and 22b are interposed between cover 22 and rotor 11 to seal against release of biohazardous materials.

The body of each of the cytocentrifuging devices 10, see FIG. 3, is preferably molded integrally from a suitable rigid plastic material, such as a high density polypropylene, to provide a chamber 23 that is open at its top for the reception of a sample of a cell-carrying liquid from which as many of the cells as possible are to be deposited on and retained by the confronting forward face of the microscope slide 13.

Slide 13 is removably inserted in a slide holder 24 which is preferably provided as part of the aforementioned clamping means and which is immediately back of a filter pad holder, here shown as a rectangular receptacle 25, into which filter pad 12 is removably inserted through top opening 25a thereof, FIG. 5 and 6.

Sample chamber 23 has depth, relative to a conduit 26 connecting it by way of a lateral outlet port 23a in a wall of such chamber with filter pad holder 25, which depth serves as a dam against outflow of the sample liquid contained by such chamber except under the influence of centrifugal force. The speed of discharge of liquid from chamber 23 is determined by the degree of slope of the forward wall 23b of such chamber. It should be noted that a damming arrangement for a chamber holding a liquid to be released only by the exercise of centrifugal force is shown by the aforementioned Wells U.S. Pat. No. 4,428,328 of Jan. 31, 1984, while inclining the damming wall 22b outwardly from the interior of the well to govern speed of liquid discharge is shown by the aforementioned N. G. Anderson "Fast Analyzer" prior art.

Conduit 26 leads from outlet port 23a of chamber 23 to the central area of filter pad holder 25. The filter pad, see 12, may be removable from and replaceable in its holder 25, as in FIGS. 1 through 6, or the filter pad may be molded or tightly inserted in an alternative form of filter pad holder as is the dual thickness filter pad 27 shown in FIGS. 7 and 8. In either event, the filter pad is provided with preferably a central opening, 12a or 27a, through which the liquid from the sample chamber must pass to reach the confronting face of the slide.

The relative magnitudes of cell sedimentation velocity and lateral liquid flow will determine whether a significant number of the cells in the sample liquid from the sample chamber will be lost to the slide by passing laterally into the filter pad before contacting, or even after contacting but failing to stick to, the confronting face of the microscope slide. To minimize loss of cells into the filter pad, the speed of sedimentation of cells onto the slide should exceed the lateral speed of travel of the liquid component into the filter pad.

To accomplish this, it is preferred that the filter pad be relatively thin marginally of the opening therethrough for liquid extracting purposes and relatively thick beyond that for liquid storing purposes. However, conventional single thickness filter pads can be used and, in both instances, a sharp circular ridge 26a may be provided, either as or on the clamping face of the clamping boss 26b, see FIG. 4, at the discharge end of conduit 26, or such clamping face of boss 26b may be left flat as in FIG. 3.

Clamping means 28 is provided for securement on rotor 11 and is preferably made as shown in, FIGS. 3 and 4. As shown, it has a pair or clamping arms 29 fixed on a shaft 30 that is rotatably inserted in and between upstanding members 31a, respectively, of base plate 31 that is fixedly secured to rotor 11, as by screws 31c, FIGS. 3 and 4, which preferably have seals such as O-rings (not shown) interposed between the rotor and the screw heads for confining biologically hazardous materials within the closed rotor. Such arms 29 are normally held in clamping position against a filter pad clamping plate 26c extending transversely from conduit 26. A pair of coil springs 32, respectively, see especially FIG. 1 on opposite end portions of shaft 30 have respective ends 32a that bear against such clamping arms 29 and force them toward and against clamping plate 26c. For relieving clamping pressure, shaft 30 is provided with a handle 33 which is fixedly secured to one end thereof for manipulation by the user when it is desired to remove device 10 from the rotor 11. In instances in which the filter pad is secured in its holding receptacle 25, as by molding the receptacle therearound as in FIGS. 7 and 8, or is inserted in and tightly held by holding receptacle 25 against removal therefrom, the entire device 10 will be removed from its base plate holder 31 in rotor 11 and discarded following deposition of the cells on the slide. Clamp 28 will remain attached to rotor 11 for reuse.

Respective recesses 25b are provided in filter-pad-holding members 25c that extend along the top and bottom of filter-pad-holding receptacle 25 to prevent scraping of cells that have been deposited on a slide 13 during centrifugation when the device 10 is removed from rotor 11 following centrifugation.

A pair of pins 26d, respectively, are provided on and extend transversely from conduit 26 in front of the clamping arms 29 to retract the device 10 from clamped position when lever 33 is depressed at such time as a centrifuging operation is completed.

The second chamber 34 is positioned above conduit 26 and has its bottom open and opening thereinto, as at 34a. It is located closer to the filter pad holder than is sample chamber 23. The open tops of both the chambers 23 and 34 are normally tightly closed, after being filled with their respective liquids, by an elongate insertable cap 35.

A filter pad wetting liquid, e.g. saline solution, is placed into chamber 34 which is sized to receive only a few droplets of the wetting liquid, typically two-hundred microliters, so surface tension will prevent movement backward or forwardly in conduit 26 of such wetting liquid except under centrifugal force when such liquid will flow toward and into the opening 12a or 27a of the filter pad in advance of the liquid sample from chamber 23.

It should be noted that, contrary to instances in which prewetting liquid has been applied to filter pads of prior art cytocentrifuges, there is here application of the prewetting liquid as part of a continuing run of the centrifuge both for prewetting the filter and for forming a barrier between the cell-carrying sample liquid and the filter pad.

When a third chamber 36, FIG. 4, similar to chamber 23, is provided in series with chambers 23 and 34, the forward chamber 34 will be used for prewetting solution, while chamber 23 will be used for the sample liquid and the final chamber 36 will be used for a fixative solution, such as fifty percent aqueous alcohol, for fixing the cells onto the slide.

The filter pad 27 of FIGS. 7 and 8 is conveniently made by compressing the marginal area of a thicker than usual filter pad sheet material to form a relatively thin and dense portion 27b circumferentially of the central opening 27a and a relatively thick and porous portion 27c for the remainder of the filter pad, but can be made by placing two together.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. For use in a cytocentrifuge having centrifuging means, a device for depositing cells from a cell-carrying liquid on a microscope slide under centrifugal force, comprising holding means for a filter pad that has a liquid-flow opening therethrough; a conduit leading to and terminating in a discharge end at said holding means which is adapted to press a filter pad against a slide about a circumferential area marginal to the liquid-flow opening in the filter pad; and at least two liquid-receiving chambers serially related along and having respective discharge ports opening into said conduit, said chambers being adapted to sequentially discharge liquid into said conduit.

2. A cytocentrifuge device according to claim 1, wherein the holding means is a filter-pad-holding receptacle having filter-pad-holding members along its bottom and top.

3. A cytocentrifugation device according to claim 2, wherein the filter-pad-holding members are recessed along a portion of their lengths somewhat longer than the width of the discharge end of the conduit to prevent the wiping off of cells from the confronting face of a slide held by slide-clamping means of a rotor on which the device is adapted to be mounted.

4. A cytocentrifugation device according to claim 2, including a filter pad held by the holding means, said filter pad having a relatively thin circumferential portion marginal to said opening with the remaining portion thereof being relatively thick as a reservoir for liquid taken up by the filter pad.

5. A cytocentrifugation device according to claim 2, wherein there is a clamping plate affixed to the conduit transversely immediately back of its discharge end thereof as part of the filter-pad-holding means for fitting into the filter pad receptacle against a filter pad therein; and wherein said filter-pad-holding means has snap-in means for receiving and holding said clamping plate.

6. A cytocentrifugation device according to claim 1, wherein the discharge end of the conduit is formed as a ridged ring for clamping against a filter pad in the filter-pad-holding means.

7. For use in a cyatocentrifuge equipped with centrifuging means, a cyatocentrifuge device for receiving a plurality of different liquids including a cell-carrying liquid whose cells are to be deposited on a microscope slide under centrifugal force, comprising holding means for a filter pad having a liquid flow opening therethrough; a liquid-receiving chamber; a conduit extending from communication with and laterally of said chamber to said holding means for discharging liquid from said chamber against a confronting face of a microscope slide upon the application of centrifugal force to said device, said chamber having depth below said communication with the conduit such as to define well that dams discharge of liquid from said chamber except by the action of centrifugal force on the liquid within said chamber; and at least one other liquid-receiving chamber positioned substantially in line with the first-mentioned chamber and above said conduit with its bottom end open and opening into said conduit, said chambers being serially related along said conduit for sequentially discharging liquid into said conduit.

8. A cytocentrifugation device according to claim 7, wherein the one other liquid-receiving chamber is for the purpose of receiving a filter-pad-wetting liquid and is located closer to the holding means than any other chamber.

9. A cytocentrifugation device according to claim 7, wherein there is another liquid-receiving chamber located substantially in line with the said first-mentioned chamber and with the said at least one other chamber.

10. A cytocentrifugation device according to claim 9, wherein the said another liquid-receiving chamber has a depth defining a dam as does the said first-mentioned chamber.

11. A cytocentrifugation device according to claim 10, wherein the said another liquid-receiving chamber is located next in line to the said first-mentioned chamber.

12. A cytocentrifugation device according to claim 7, wherein the conduit is substantially horizontal so that any liquid discharged thereinto from said at least one other chamber, except under the influence of centrifugal force, will be prevented by surface tension from flowing either forwardly or backwardly.

13. A cytocentrifugation method of depositing and adhering cells onto a microscope slide, comprising the steps of placing a cell-carrying liquid sample in a chamber of an in-line series of chambers extending along and opening into a conduit, in a cytocentrifugation device of cytocentrifuging apparatus, that leads to and terminates at filter-pad-holding means in which a filter pad is held circumferentially and marginally of an opening in said filter pad, through which opening said liquid sample is passed under centrifuging conditions; placing a filter-pad-prewetting liquid in a chamber of said series of chambers that is first in line toward said filter-pad-holding means and that precedes in line said chamber in which said cell-carrying liquid sample is placed; and operating said cytocentrifuging apparatus.

14. A cytocentrifuging method according to claim 13, comprising the additional step of placing a cell-fixative solution in a chamber of the series of chambers that is next in line following the chamber in which the cell-carrying liquid sample is placed; and then operating said cytocentrifuging apparatus.

* * * * *

UNITED STATES PATENT AND TRADEMARK OFFICE
CERTIFICATE OF CORRECTION

PATENT NO. : 5,252,228

DATED : October 12, 1993

INVENTOR(S) : Barry O. Stokes; Carmelo G. Quirante

It is certified that error appears in the above-identified patent and that said Letters Patent is hereby corrected as shown below:

Column 4, line 51, change "us" to --use--.

Column 8, line 49, before "well", insert --a--.

Signed and Sealed this

Fourteenth Day of June, 1994

Attest:

BRUCE LEHMAN

*Attesting Officer*  *Commissioner of Patents and Trademarks*